United States Patent
Karavas et al.

(10) Patent No.: US 9,943,483 B2
(45) Date of Patent: Apr. 17, 2018

(54) PREPARATION OF PEPTIDE LOADED PLGA MICROSPHERES WITH CONTROLLED RELEASE CHARACTERISTICS

(71) Applicant: PHARMATHEN S.A., Pallini-Attikis (GR)

(72) Inventors: Evangelos Karavas, Pallini Attikis (GR); Efthymios Koutris, Pallini Attikis (GR); Katerina Minioti, Pallini Attikis (GR); Sotiria Chaitidou, Pallini Attikis (GR); Georgia Papanikolaou, Pallini Attikis (GR); Theofanis Mantourlias, Pallini Attikis (GR)

(73) Assignee: PHARMATHEN S.A., Pallini, Attikis (GR)

(*) Notice: Subject to any disclaimer, the term of this patent is extended or adjusted under 35 U.S.C. 154(b) by 0 days.

(21) Appl. No.: 15/124,587

(22) PCT Filed: Mar. 31, 2014

(86) PCT No.: PCT/EP2014/000858
§ 371 (c)(1),
(2) Date: Sep. 8, 2016

(87) PCT Pub. No.: WO2015/149820
PCT Pub. Date: Oct. 8, 2015

(65) Prior Publication Data
US 2017/0281547 A1    Oct. 5, 2017

(51) Int. Cl.
*A61K 9/16*    (2006.01)
*A61K 38/31*    (2006.01)
*A61K 9/00*    (2006.01)

(52) U.S. Cl.
CPC .......... *A61K 9/1647* (2013.01); *A61K 9/0019* (2013.01); *A61K 38/31* (2013.01)

(58) Field of Classification Search
CPC .................................................. A61K 9/1647
See application file for complete search history.

(56) References Cited

U.S. PATENT DOCUMENTS

| | | |
|---|---|---|
| 6,902,743 B1 | 6/2005 | Setterstrom et al. |
| 6,913,767 B1 | 7/2005 | Cleland et al. |
| 2010/0086597 A1 | 4/2010 | Woo et al. |

FOREIGN PATENT DOCUMENTS

| | | |
|---|---|---|
| WO | 01/10414 A1 | 2/2001 |
| WO | 0110414 A1 * | 2/2001 |
| WO | 2005/110369 A2 | 11/2005 |

OTHER PUBLICATIONS

Jeyanthi R. et al, Effect of solvent removal technique on the matrix characteristics of polylactide/glycolide microspheres for peptide delivery, Journal of Controlled Release, Elsevier Amsterdam, NL, vol. 38, No. 2, Feb. 1, 1996, p. 235-244, Entire Document.

(Continued)

*Primary Examiner* — Carlos A Azpuru
(74) *Attorney, Agent, or Firm* — AKC Patents, LLC; Aliki K. Collins

(57) ABSTRACT

A novel process for the preparation of a long acting injectable composition based on biodegradable poly(D,L-lactide-co-glycolide) microspheres comprising peptide active pharmaceutical ingredients.

7 Claims, 12 Drawing Sheets

(56) References Cited

OTHER PUBLICATIONS

Mehta R C et al, "Biodegradable microspheres as depot system for parenteral delivery of peptide drugs" Journal of Controlled Release, Elsevier Amsterdam, NL, vol. 29, No. 3, Mar. 1, 1994, p. 375-384, Entire Document.

* cited by examiner

Formulation 1a

Formulation 1b

Formulation 1c

Formulation 2a

Formulation 2b

Formulation 2c

PREPARATION OF PEPTIDE LOADED PLGA MICROSPHERES WITH CONTROLLED RELEASE CHARACTERISTICS

TECHNICAL FIELD OF THE INVENTION

The present invention relates to preparation of biodegradable poly(D,L-lactide-co-glycolide) "PLGA" microspheres comprising peptide active pharmaceutical ingredients and how to achieve controlled release characteristics. In particular, the present invention relates to emulsion solvent extraction/evaporation method where the release of peptide from the polymer matrix is controlled by the temperature profile during the solvent evaporation step.

BACKGROUND OF THE INVENTION

Peptide drugs are usually administered systemically, e.g. parenterally due to their poor oral absorption and high instability in gastric fluids. However, parenteral administration may be painful and cause discomfort, especially for repeated daily administrations. In order to minimize the number of injections to a patient, the drug substance is advantageously administered as a depot formulation. The parenteral administration of peptide drugs as a depot formulation in a biodegradable polymer, e.g. as microspheres or implants, has been proposed enabling their sustained release after a residence time in the polymer which protects the peptide against enzymatic and hydrolytic influences of the biological media. A common drawback with injectable depot formulations is the fluctuation in plasma levels such as high peak levels which cause undesired pharmacological side reactions together with plasma levels close to zero during the entire release period. A therapeutically relevant blood level over an extended period of time is difficult to achieve and satisfactory peptide release profiles are in practice only obtained in very few cases.

Identified factors that control the peptide release characteristics of a parenteral depot in the form of PLGA microspheres include peptide form (i.e., free peptide, salt form), polymer type (i.e., molecular weight, lactide to glycolide ratio, linear or branched structure, end-terminal groups), drug loading, particle size and particle porosity and the distribution of the drug into the polymer matrix (U.S. Pat. No. 5,538,739).

Few commercial long-acting release drug formulations of microspheres are available on the market. SANDOSTATIN LAR® is a commercial available parenteral depot formulation comprising octreotide acetate active peptide. It is indicated for, inter alia, long-term maintenance therapy in acromegalic patients, and treatment of severe diarrhea and flushing associated with malignant carcinoid tumors and vasoactive intestinal peptide tumors (vipoma tumors). Approved at doses of 10, 20 and 30 mg (and up to 40 mg for patients with acromegaly in certain countries such as the US and Japan), Sandostatin LAR® allows for once-monthly intragluteal injection. The pharmacokinetic profile of octreotide after injection of Sandostatin LAR® reflects the release profile from the polymer matrix and its biodegradation. After a single i.m. injection in humans, the octreotide concentration reaches a transient initial peak within 1 hour after administration, followed by a progressive decrease to a low undetectable level within 24 hours. After this initial release on day 1, octreotide remains at sub-therapeutic levels in the majority of the patients for the following 7 days. Thereafter, octreotide concentration increases again and around day 14 (about 2-3 weeks post-injection) reaches plateau levels which are maintained during the following 3 to 4 weeks, then a decline period of 6 weeks follows (Summary of product characteristics for Sandostatin LAR® 10 mg, 20 mg or 30 mg powder and solvent for suspension for intramuscular injection, 2013). In agreement with the above and according to the available literature data the expected release profile for Sandostatin LAR in rats follows the same pattern (AAPS PharmSciTech, Vol. 12, No 4 (2011)).

There are a number of techniques for the microencapsulation of peptides in PLGA microspheres. The most widely used techniques both in lab scale and for commercial productions include phase separation/coacervation technique, spray drying and single or double emulsion/solvent evaporation technique (PDA J Pharm Sci and Tech 2008, 62 125-154; Microencapsulation Methods and Industrial Applications Second Edition).

1. In phase-separation or coacervation technique, an aqueous solution of peptide/protein is emulsified or alternatively the peptide/protein is dispersed in solid form into solution containing dichloromethane and PLGA. Silicone oil is added to this dispersion at a defined rate, reducing solubility of polymer in its solvent. The polymer-rich liquid phase (coacervate) encapsulates the dispersed peptide/protein molecules, and embryonic microspheres are subjected to hardening and washing using heptane. The process is quite sensitive to polymer properties, and residual solvent is also an important issue.

2. In spray-drying technique a polymer is dissolved in a volatile organic solvent such as dichloromethane or acetone. The protein is suspended as solid or emulsified as aqueous solution in this organic solution by homogenisation. After that, the resulting dispersion is atomised through a (heated) nozzle into a heated air flow. The organic solvent evaporates, thereby forming microspheres with dimensions of typically 1-100 m. The microspheres are collected in a cyclone separator. For the complete removal of the organic solvent, a vacuum-drying or lyophilization step can follow downstream. The internal structure of the resulting polymeric microspheres depends on the solubility of the peptide/protein in the polymer before being spray-dried leading to the formation of reservoir or matrix type products. When the initial dispersion is solution, the final product obtained following spray drying is matrix or monolithic type, that is, polymer particles with dissolved or dispersed nature of the active ingredient (defined as microspheres). Conversely, when the initial dispersion is in suspension, the product obtained is reservoir type, that is, a distinct polymeric envelope/shell encapsulating a liquid core of dissolved active ingredient (defined as microcapsules).

3. Oil-in-water (o/w) and water-in-oil-water (w/o/w) are the two hydrous techniques representing, respectively the single and double emulsion formation during microspheres preparation. In these processes, peptides/proteins are dissolved in an organic solvent (e.g., alcohol) or in an aqueous solution and then mixed or emulsified with an organic solution (non-miscible with water) of the polymer to form a solution or water-in-oil (w/o) emulsion, respectively. Dichloromethane serves as organic solvent for the PLGA and the o/w primary emulsion is formed using either high-shear homogenization or ultrasonication. This primary emulsion is then rapidly transferred to an excess of aqueous medium containing a stabilizer, usually polyvinyl alcohol (PVA). Again homogenization or intensive stirring is necessary to initially form a double emulsion of w/o/w. Subsequent removal (by evaporation) of organic solvent by heat, vacuum, or both results in phase separation of polymer and core to produce microspheres. Instead of solvent evaporation, solvent extraction with large quantity of water with or without a stabilizer can also be undertaken to yield microspheres containing peptide/protein. Although the w/o/w microencapsulation technique seems to be conceptually simple to carry out, the particle formation process is quite complicated, and a host of process parameters are having an influence on or affect the properties of peptide/protein-loaded PLGA microspheres.

Until now the temperature profile as applied during the evaporation step in emulsion/solvent evaporation techniques has not been identified as a critical process parameter to affect the release characteristics of the peptide from the polymer matrix. On the contrary, processing under constant temperature slightly above the boiling point of the organic solvent is generally applied (or slightly above the vapour pressure of the solvent when a reduced pressure/vacuum is applied to accelerate the evaporation of the solvent).

A typical release mechanism for these types of formulations includes three phases that can be generally represented as the initial release phase (phase 1), the hydration phase (phase 2), and primary release phase (phase 3) that is diffusion controlled but facilitated by erosion of the polymer matrix. The drug release begins after a lag time when the polymer molecular weight falls below a critical value and thus mass loss can take place (Faisant N, Siepmann J, Benoit J P. PLGA-based microspheres: elucidation of mechanisms and a new, simple mathematical model quantifying drug release. Eur J Pharm Sci. 2002 May; 15(4):355-66; Körber M. PLGA erosion: solubility- or diffusion-controlled? Pharm Res. 2010 November; 27(11):2414-20). There is a need in the art for an improved manufacturing method to control the release profile of the peptide drug substance from the polymer matrix of the microspheres.

SUMMARY OF THE INVENTION

The present invention relates to single or double emulsion/solvent evaporation technique for the preparation of sustained release PLGA microspheres comprising peptide drugs, in particular Octreotide, where the release of the peptide from the polymer matrix is controlled by the temperature profile applied during the solvent evaporation step. Other peptides include; exenatide, leuporelin, goserelin, liraglutide and teduglutide, In one aspect, the present invention relates to a method where solvent evaporation step is conducted under a controlled temperature which rises in temperature during the evaporation step to result in the solidification of microspheres. The resulting microspheres are collected by sieving, washed and finally dried under vacuum in a filter dryer to provide free-flowing powder.

We present as a feature of the invention a process for the preparation of a poly(D,L lactide-co-glycolide) polymer microspheres of a peptide, which peptide can also be in the form of a pharmaceutically-acceptable salt, comprising:

a. dissolving the peptide, or salt thereof, in at least one organic solvent miscible in water, and optionally containing also water, to form a water phase;
b. forming an oil-in-water or water-in-oil-water emulsion in a suitable oil phase comprising an organic solution of the poly(D,L lactide-co-glycolide) polymer, the solution being non-miscible with the water phase;
c. evaporating the at least one organic solvent used in a. from the emulsion to form the microspheres by controlling the temperature during the evaporation step and increasing the temperature during the evaporation step.

In a further aspect, the release characteristics of the microspheres, as proved by in-vitro and in vivo data, is controlled by the degree of temperature increasing during the solvent evaporation step. More particularly, the temperature during the solvent evaporation by increasing the temperature from a starting temperature of from 15 to 25° C., preferably about 20° C. Preferably the maximum temperature achieved is up to 38° C. or 380. The temperature is raised over a time period of 20 min to 3 hours. Drying may continue for an extended period after the period of temperature elevation. Preferably the rate of temperature increase is 0.1° C./min-1° C./min. The temperature rise may be constant over the period or staged. By staged we mean that each change is a step change in temperature and then that temperature is held for a period before the next change. There can also be a mixture of staged and constant temperature changes during the evaporation stage.

By the term "release characteristics" we mean the dissolution profile of the formulations in a method that correlates with the in vivo PK profile of the formulations in rats after a single intramuscular injection. In one aspect, a type A in vitro in vivo correlation has been established between the in vitro dissolution profile and the in vivo release profile as calculated from the deconvolution of the plasma concentration curves in rats by applying a one compartment model.

More particularly, "dissolution profile" refers to the quantity or amount of octreotide that is released from the microspheres as a function of time in acetate buffer 1 mM pH 4.0 at 37° C.

The release characteristics are expressed by the initial burst (phase 1), the lag-time (phase 2) and the duration and slope of the of the primary release phase (phase 3). More particularly, the dissolution profile is fitted by the following equation where the constant $y_o$ reflects the initial burst, the constant $x_o$ reflects the lag-time and the constants a and b describe the primary release phase.

$$\% \text{ Release} = y_o + \frac{a}{1 + \exp\left(\frac{-(x - x_0)}{b}\right)}$$

The present invention relates to an emulsion (single or double)/solvent evaporation method for the preparation of PLGA microspheres comprising a pharmaceutical active peptide where the temperature-increasing rate during the solvent evaporation step is used to control the release characteristics of the enclosed peptide. More particularly, the rate of temperature increase during the solvent evaporation phase is used to control the lag-time of the peptide release profile that is expressed by the calculated $x_o$ constant of the dissolution profile of the microspheres. The lag-time of the release profile of the resulting microspheres is tested in acetate buffer 1 mM pH 4.0 at 37° C.

More particularly, the single emulsion/solvent evaporation technique includes the following steps (FIG. 1):

i. Octreotide is dissolved in an appropriate amount of suitable solvent, preferably methanol ii. Poly(D,L-lactide-co-glycolide) polymer is dissolved in dichloromethane and the solution is cooled down to 10° C. or below, preferably 5° C. or below.
iii. The two solutions are mixed together under vigorous stirring to form the dispersed said oil phase
iv. The aqueous, said continuous phase is made by dissolving disodium hydrogen phosphate and potassium dihydrogen phosphate in a PVA solution and cooled down to 10° C. or below, preferably 5° C. or below.
v. The dispersed and the continuous phases are mixed together, preferably using an in-line high shear disperser, forming semi-solid microspheres of desired particle size distribution. The flow of the continuous phase is achieved by a peristaltic pump whereas the flow of the ratio of continuous is achieved by a syringe pump
vi. The formed microspheres are transferred from the outlet to a suitable vessel controlled at between 15 and 25° C., preferably about 20° C., under stirring
vii. The hardening of the microspheres is achieved by gradually increasing the as described herein
viii. After several hours of total drying, about 4, the dried microspheres are transferred to a filter dryer
ix. The particles are washed in the filter dryer with water, preferably at room temperature, and after draining the microspheres are left to dry for at least 12 hours, preferably 24 hours, preferably under 10 mbar vacuum and gently stirring Accordingly the double emulsion/solvent evaporation technique includes the following steps (FIG. 2):
i. Octreotide is dissolved in an appropriate amount of water
ii. Poly(D,L-lactide-co-glycolide) polymer is dissolved in dichloromethane and the solution is cooled down to 10° C. or below, preferably 5° C. or below.
iii. The two solutions are emulsified, preferably at 20.000 rpm for 1 minute using a digital T25 ULTRA-TURRAX top mounted disperser forming the dispersed said oil phase. and cooled down to 10° C. or below, preferably 5° C. or below.
iv. The aqueous continuous phase is made by dissolving disodium hydrogen phosphate and potassium dihydrogen phosphate in a PVA solution and cooled down to 10° C. or below, preferably 5° C. or below.
v. The dispersed and the continuous phases are mixed together, preferably using an in-line high shear disperser, forming semi-solid microspheres of desired particle size distribution. The flow of the continuous phase is achieved by a peristaltic pump whereas the flow of the ratio of continuous is achieved by a syringe pump
vi. The formed microspheres are transferred from the outlet to a reactor vessel controlled at between 15 and 25° C., preferably about 20° C., under stirring
vii. The hardening of the microspheres is achieved by gradually increasing the as described herein
viii. After several hours of total drying, about 4, the dried microspheres are transferred to a filter dryer
ix. The particles are washed in the filter dryer with water, preferably at room temperature, and after draining the microspheres are left to dry for at least 12 hours, preferably 24 hours, preferably under 10 mbar vacuum and gently stirring

DETAILED DESCRIPTION OF THE INVENTION

Figure 1A:
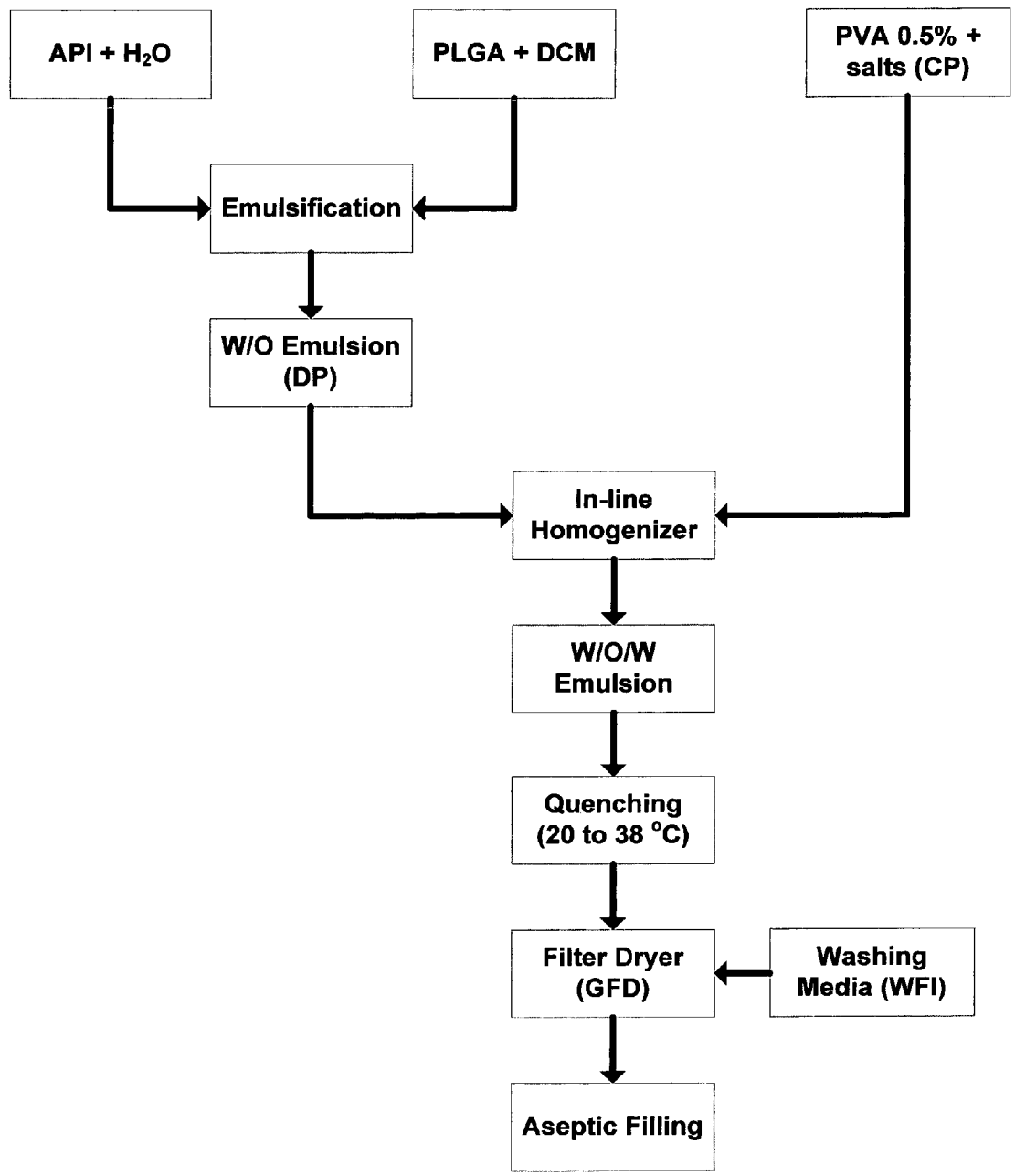
FIG. 1a: Schematic diagram of the double emulsification process
Figure 1B:
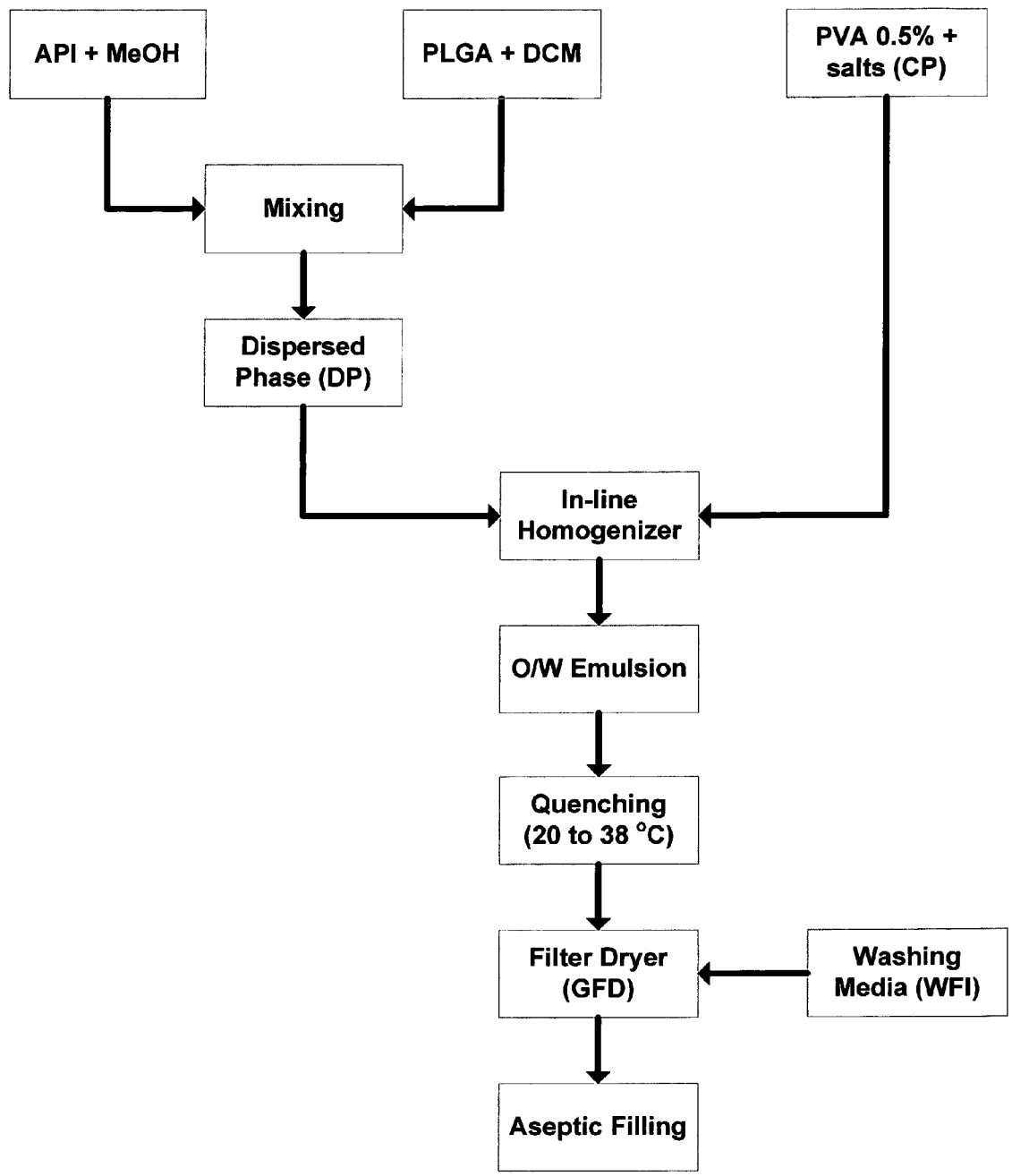
FIG. 1b: Schematic diagram of the single emulsification process
Figure 2A:
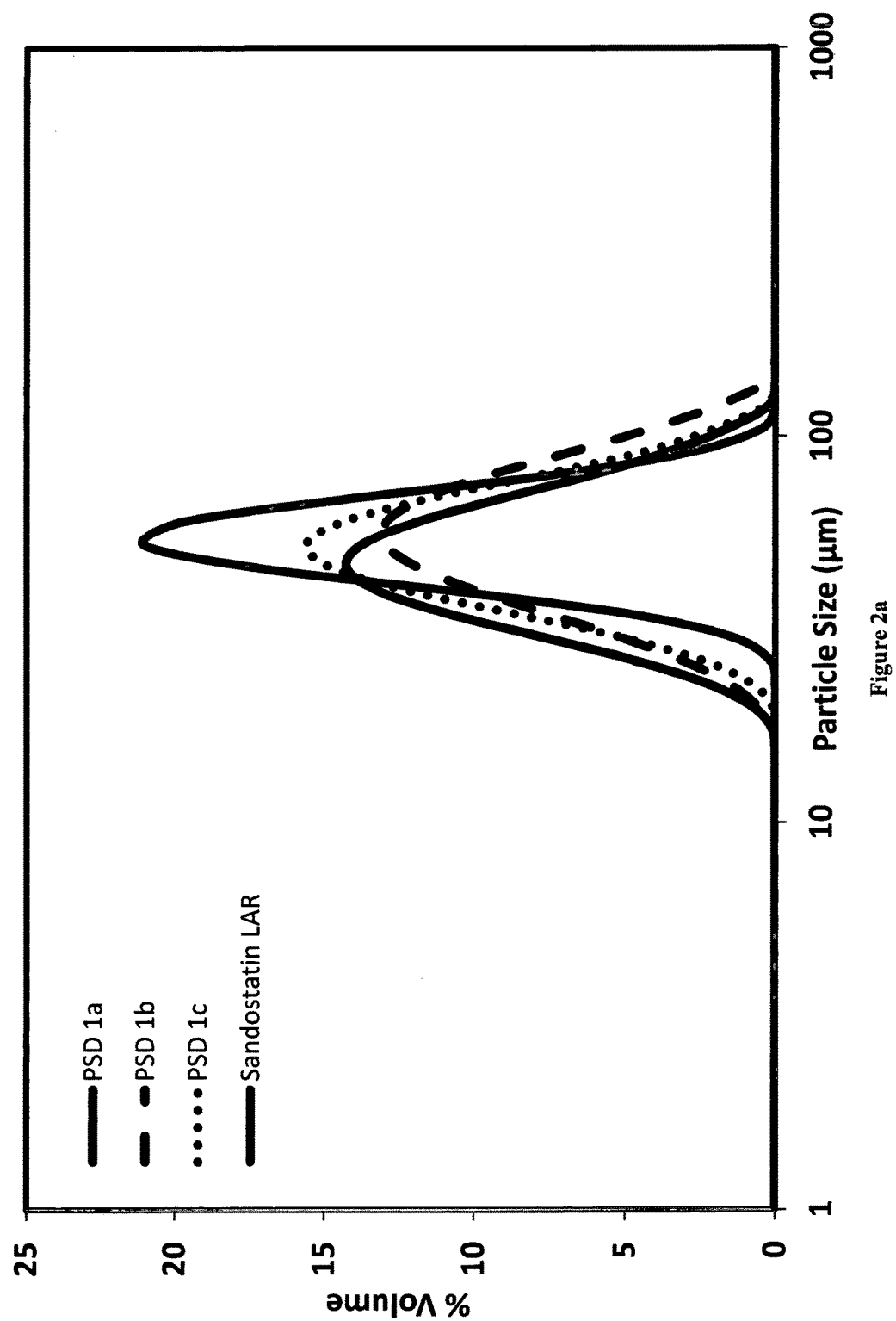
FIG. 2a: Particle size distribution graph for the formulations 1a-1c
Figure 2B:
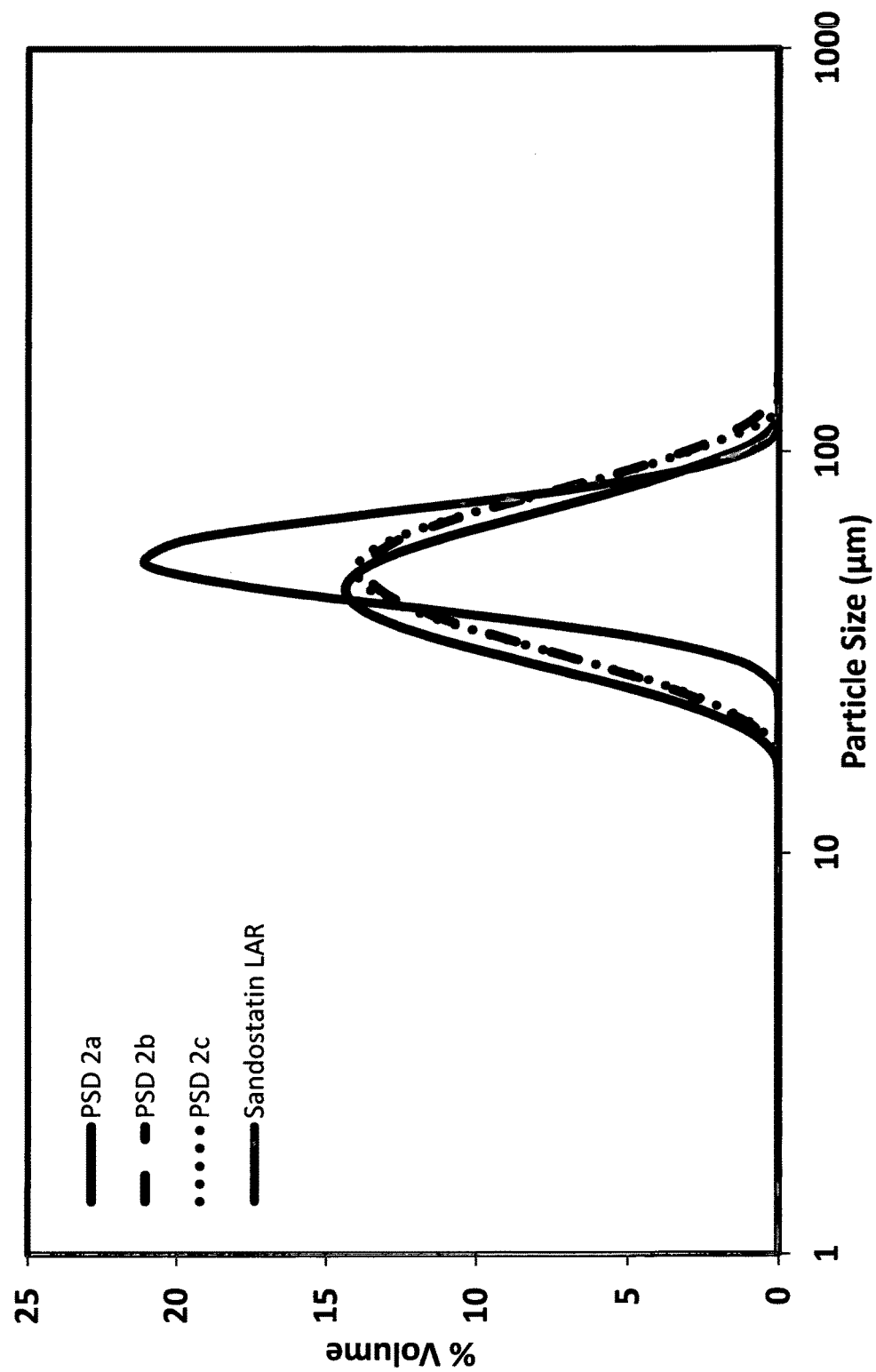
FIG. 2b: Particle size distribution graph for the formulations 2a-2c
Figure 3A:
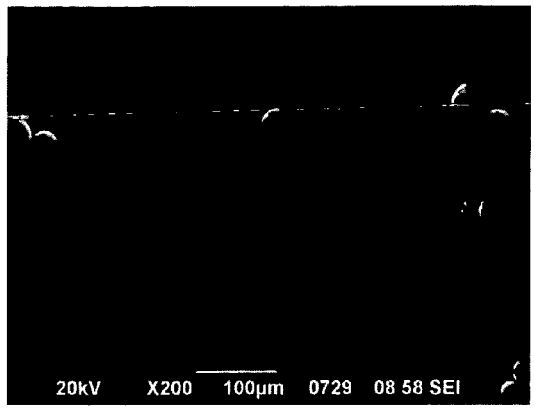
FIG. 3a: SEM and crosssectional SEM images of the formulations 1a-1c
Figure 3A:
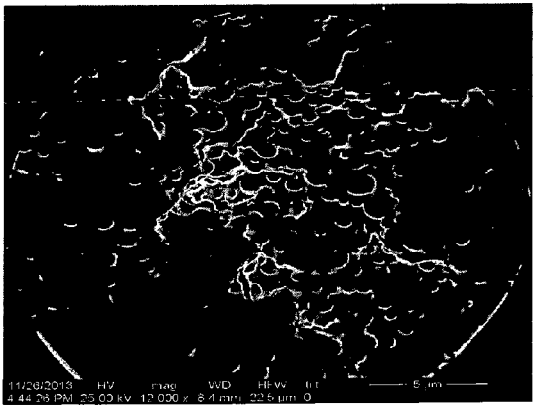
Figure 3A:
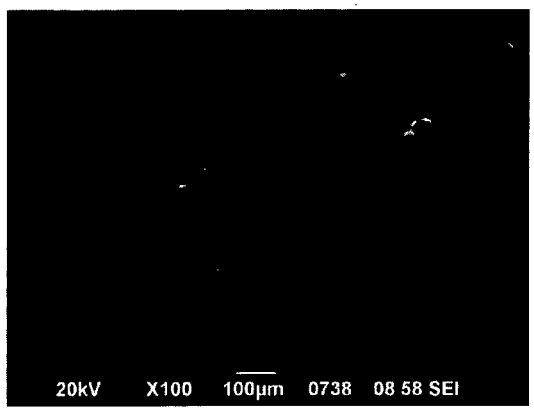
Figure 3A:
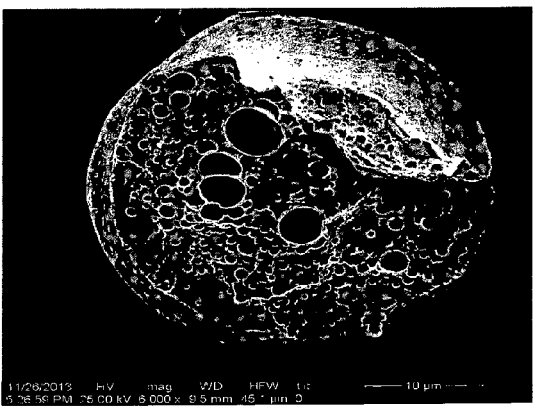
Figure 3A:
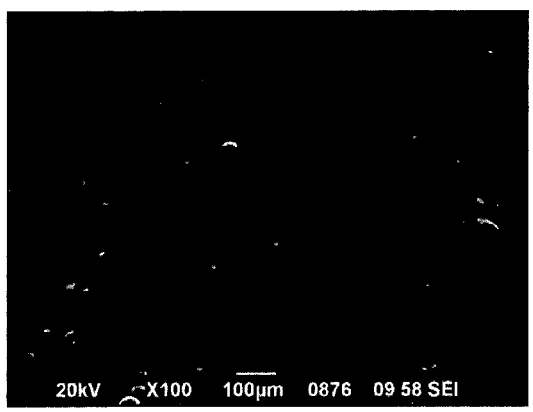
Figure 3A:
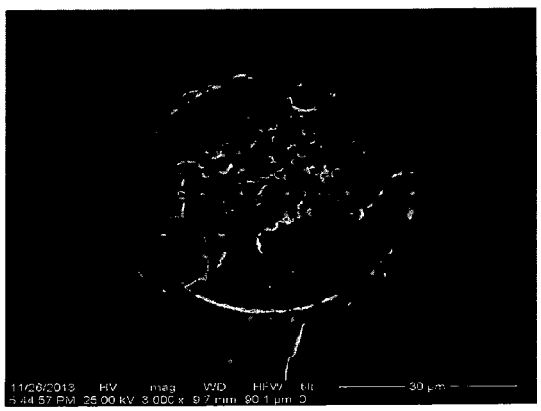
Figure 3B:
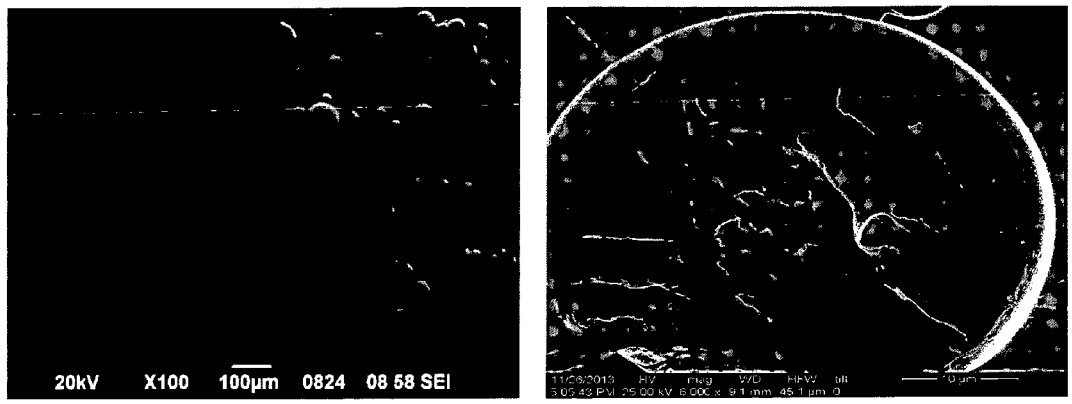
FIG. 3b: SEM and crosssectional SEM images of the formulations 2a-2c
Figure 3B:
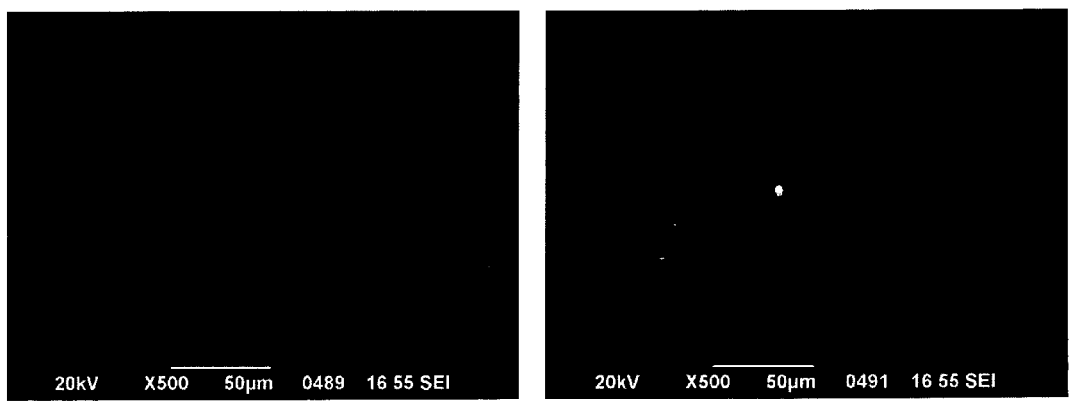
Figure 3B:
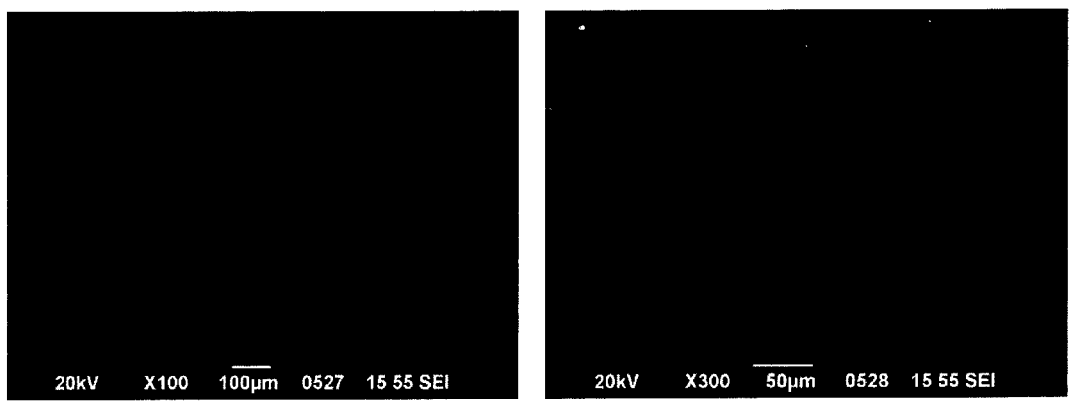

The present invention provides a sustained release formulation of octreotide acetate with release characteristics controlled by the controlling and increasing the temperature during the solvent evaporation step of the manufacturing process.

Octreotide (also known as (4R,7S,10S,13R,16S,19R)-19-[(2R)-2-amino-3-phenylpropanamido]-10-(4-aminobutyl)-16-benzyl-N-[(2R,3R)-1,3-dihydroxybutan-2-yl]-7-(1-hydroxyethyl)-13-(1H-indol-3-ylmethyl)-6,9,12,15,18-pentaoxo-1,2-dithia-5,8,11,14,17-pentaazacycloicosane-4-carboxamide, preferably in the form of the acetate salt (or any other pharmaceutically-acceptable salt) or also known as 4D-phenylalanyl-L-cysteinyl-L-phenylalanyl-D-tryptophyl-L-lysyl-L-threonyl-N-((1R,2R)-2-hydroxy-1-(hydroxymethyl)propyl)-L-cysteinamide cyclic (2-7)-disulfide acetate (salt) or L-Cysteinamide-D-phenylalanyl-L-cysteinyl-L-phenylalanyl-D-tryptophyl-L-lysyl-L-threonyl-N-(2-hydroxy-1-(hydroxymethyl)propyl)-cyclic(2-7)-disulfide (R—(R*,R*)), acetate (salt)) is a synthetic octapeptide (DPhe-Cys-Phe-DTrp-Lys-Thr-Cys-Thr-ol) analogue of the naturally occurring hormone somatostatin, and is approved for use in tumor control in neuroendocrine disorders such as acromegaly and gastroenteropancreatic neuroendocrine tumors. The chemical structure of octreotide acetate is shown below:

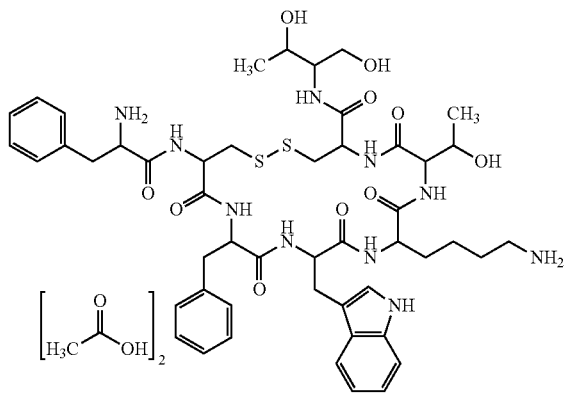

Suitable commercially obtainable polymers for use in preparing of PLGA microspheres according to the present invention include but are not limited to RESOMER® and LAKESHORE BIOMATERIALS by Evonik Industries AG, Expansorb® by PCAS., PURASORB® by PURAC Biochem BV. The PLGA polymers used in the present invention may have a ratio of lactic acid and glycolic acid in the range of about 50:50 to about 65:35 and a weight average molecular weight (Mw) in the range of 10,000 to 70,000. Preferably the present invention uses PLGA having a monomer ratio of 50:50 and a weight average molecular weight in the range of 30,000-50,000.

Organic solvents for the PLGA that can be used in the present invention include but not limited to ethylacetate, tetrahydrofurane, acetonitrile, dichloromethane, hexafluoroisopropanol, chloroform and acetone. More preferably, in the present invention dichloromethane is used. The polymer concentration in the organic solvent is 10-40% wt., most preferably 20-30% wt.

In the present invention octreotide acetate is dissolved in water for injection to result in a concentration of 10-40% wt. and more preferably 25-35% wt. Alternatively octreotide acetate is dissolved in a suitable organic solvent miscible in water, preferably methanol, to result in a concentration of 5-20% wt., more preferably 10% wt. Optionally an organic solvent miscible in water with water is used.

For the preparation of the dispersed phase, the octreotide acetate solution is dispersed in the polymer solution by using a batch mode high shear disperser operating at a shear rate of 15,000-30,000 $s^{-1}$. More preferably, a shear rate of 20,000-25,000 $s^{-1}$ is applied. Alternatively, octreotide acetate solution in methanol is added in the polymer solution under stirring. The dispersed phase is controlled at a temperature of lower than 20° C., more preferably 5-10° C.

In the present invention the continuous phase consists of an aqueous solution with a surfactant, preferably polyvinyl alcohol (PVA). Examples of other surfactants that optionally can be employed include one or more; anionic surfactants (such as, sodium oleate, sodium stearate or sodium lauryl sulfate), non-ionic surfactants (such as, Poloxamers, Tweens), polyvinylpyrrolidone, carboxymethyl cellulose sodium and gelatin, used independently or in combination. PVA, preferably have a weight average molecular weight from about 10,000 to about 150,000 Da that correspond to viscosity range of 3-9 cP when measured as a 4% aqueous solution at 20° C., 85-89% degree of hydrolysis and ester number of 130-150. Selected PVA grades that are used in the present invention include Emprove PVA 4-88 (Mw 25,000-30,000; viscosity 4% in water: 3.4-4.6 cPs), PVA 8-88 (Mw about 65,000; viscosity 4% in water 6.8-9.2 cPs) and PVA 18-88 (Mw about 130,000; viscosity 4% in water) available by Merck KGaA. Amount of the surfactant added to the aqueous phase is preferably up to 5.0% (w/w) relative to mass of the aqueous solution. More preferably the amount of surfactant (optimally the PVA amount) is from about 0.5 to about 2.5% w/w. The continuous phase is thermo stated at a temperature lower than 20° C., more preferably 5-10° C.

In the present invention the emulsification of the water phase in the continuous oil phase is performed with one of the following means: i) mechanical stirring, ii) batch disperser iii) in line disperser. Preferably, the emulsification process takes place by an in-line disperser MT-3000 available by Kinematica operating at a shear rate of 5,000-20,000 $s^{-1}$, most preferably at a range of 10,000-15,000 $s^{-1}$ to result in the formation of microspheres of 10-250 μm, most preferably of 20-100 μm. The weight ratio between the dispersed and the continuous phase during is 1:20-1:150, more preferably 1:75-1:100.

The formed microsphere suspension is transferred (from the outlet of the in-line disperser) into a suitable vessel (preferably insulated to help with temperature control) which is initially controlled at above 15° C., preferably at about 20° C. The temperature during the solvent evaporation is increased from a starting temperature of from 15 to 25° C., preferably about 20° C. Preferably the maximum temperature achieved is up to 35° C. or 38° C. The temperature is raised over a time period of 20 min to 3 hours. Drying may continue for an extended period after the period of temperature elevation. Preferably the rate of temperature increase is 0.1° C./min-1° C./min. The temperature rise may be constant over the period or staged. By staged we mean that each change is a step change in temperature and then that temperature is held for a period before the next change. There can also be a mixture of staged and constant temperature changes during the evaporation stage.

The evaporation of the solvent from the microsphere takes place according to the applied temperature profile under stirring and a partial vacuum, preferably the partial vacuum is slightly below the vapour pressure of dichloromethane.

After the evaporation of the solvent the hardened particles are collected from the suspension in a filter dryer under low stirring. Preferably, a filter dryer from PSL (Powder System Limited) is used. The collected particles are washed with water and then dried in the filter dryer by applying a vacuum of about 10 mbar.

Figure 4A:
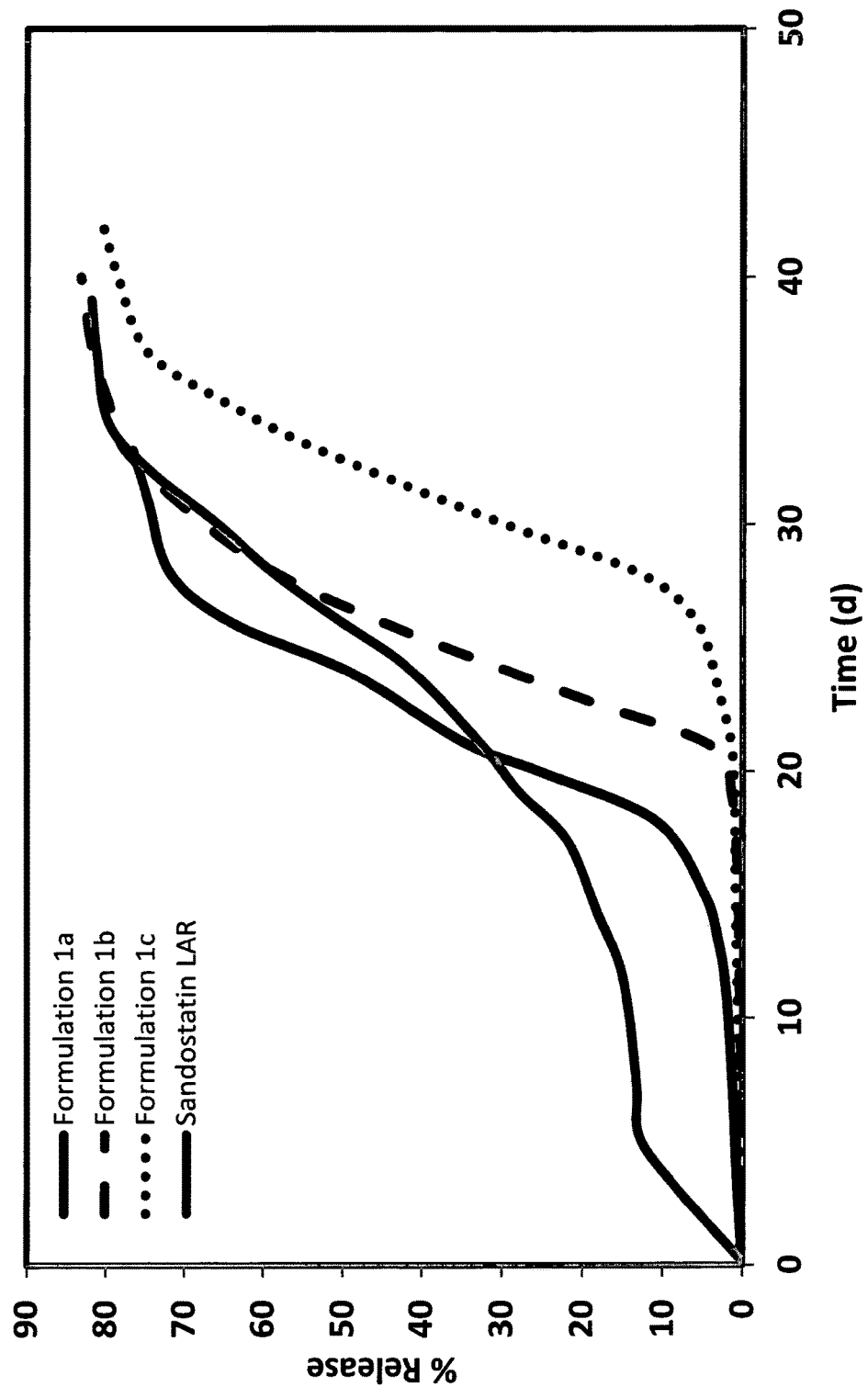
FIG. 4a: Comparative dissolution profiles of Sandostatin LAR and formulations 1a-1c
Figure 4B:
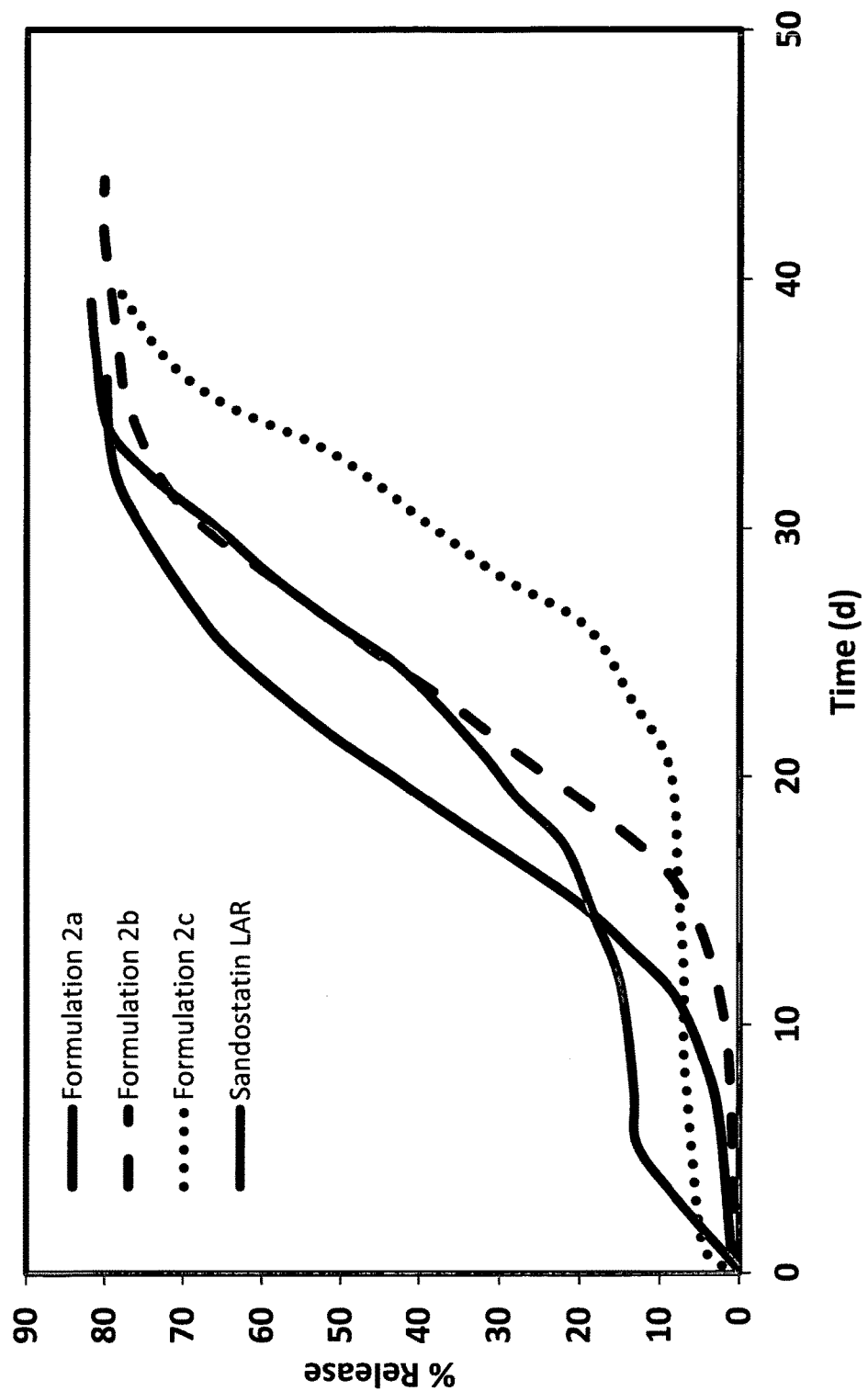
FIG. 4b: Comparative dissolution profiles of Sandostatin LAR and formulations 2a-2c
Figure 5:
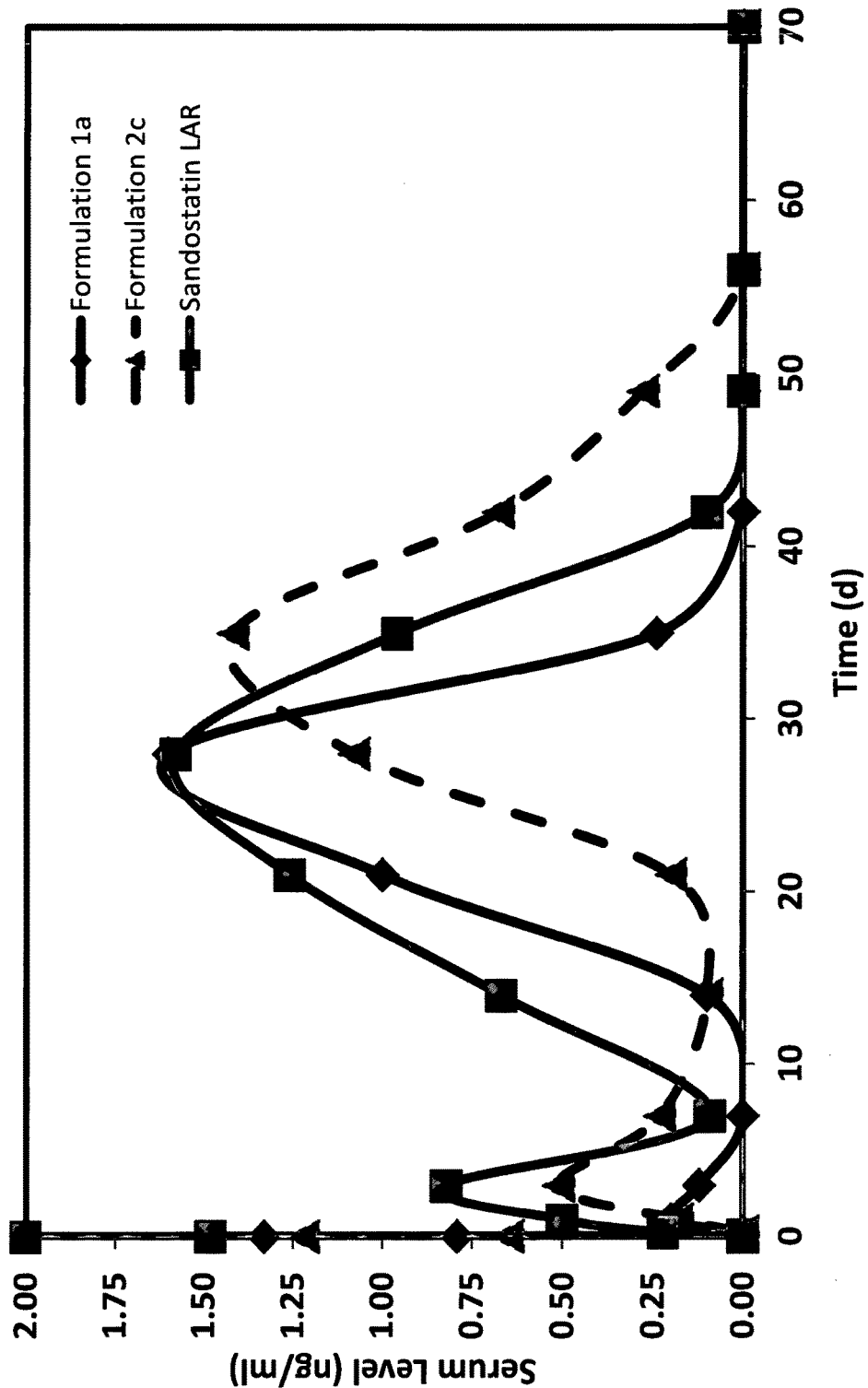
FIG. 5: Plasma concentration profiles in rats of Sandostatin LAR and formulations 1a and 2c
Figure 6A:
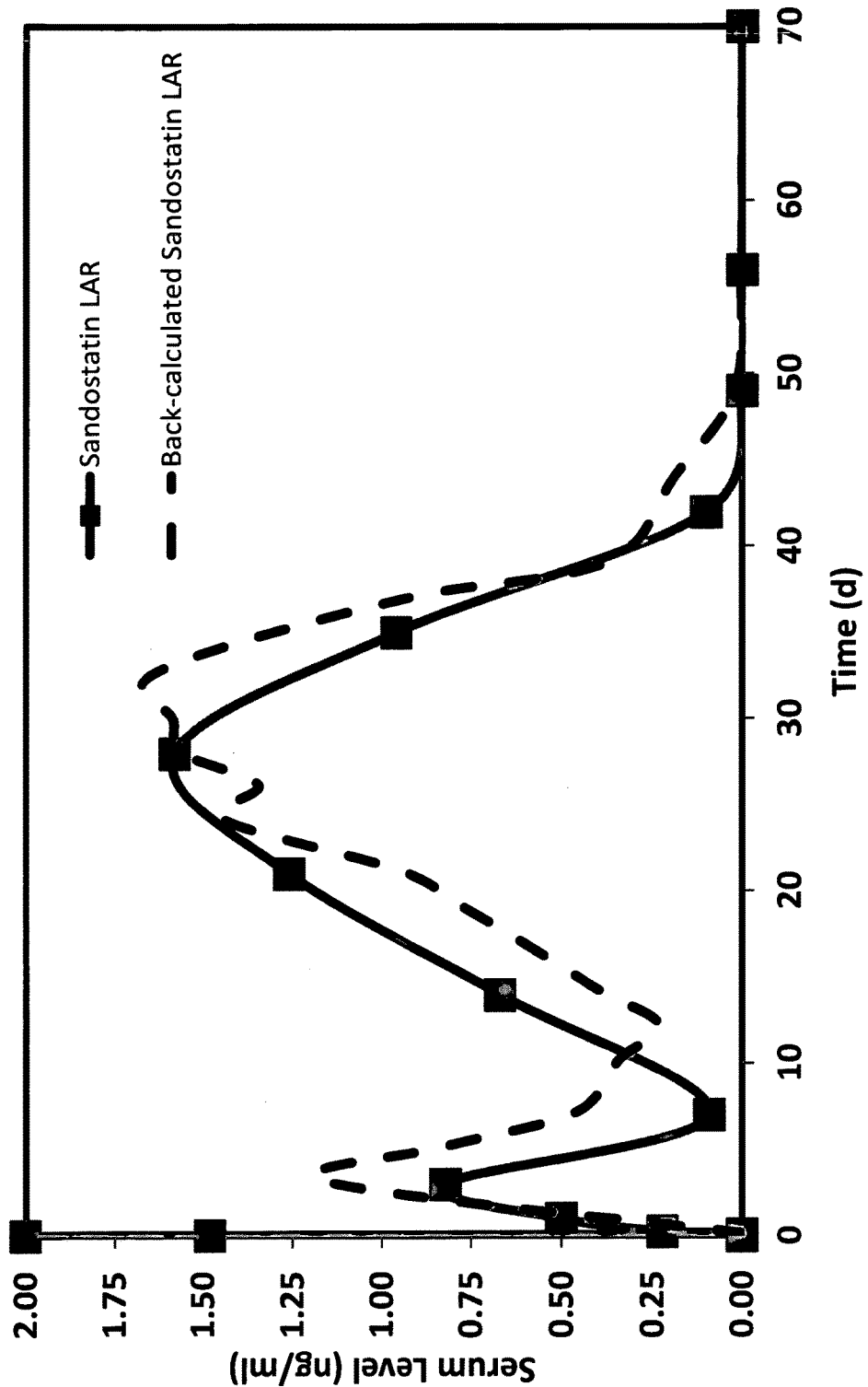
FIG. 6a: Comparison of the in vivo observed and the back-calculated plasma concentration of Sandostatin LAR
Figure 6B:
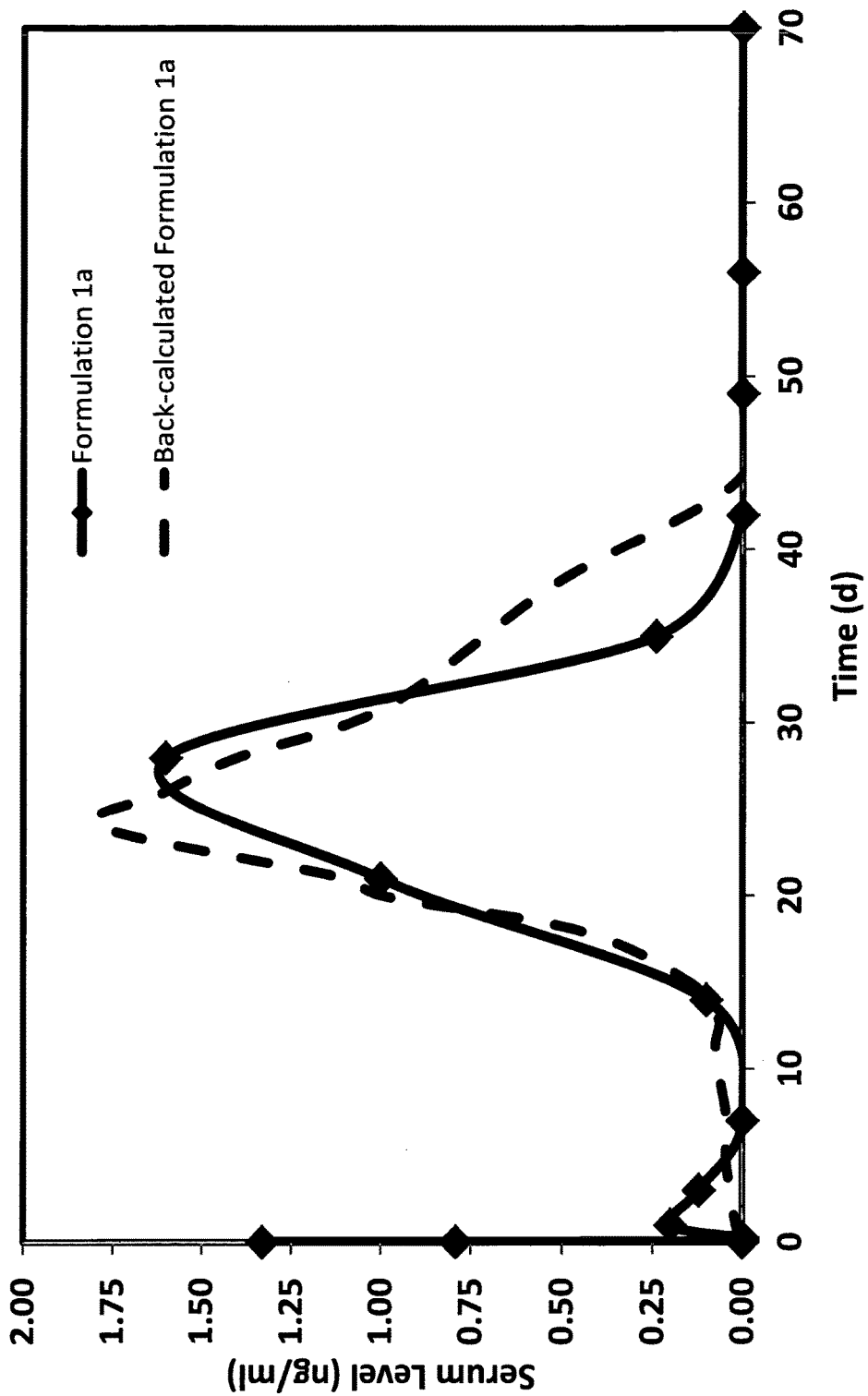
FIG. 6b: Comparison of the in vivo observed and the back-calculated plasma concentration of formulation 1a
FIG. 6c: Comparison between the observed and the predicted plasma concentration of formulation 2c
Figure 6C:
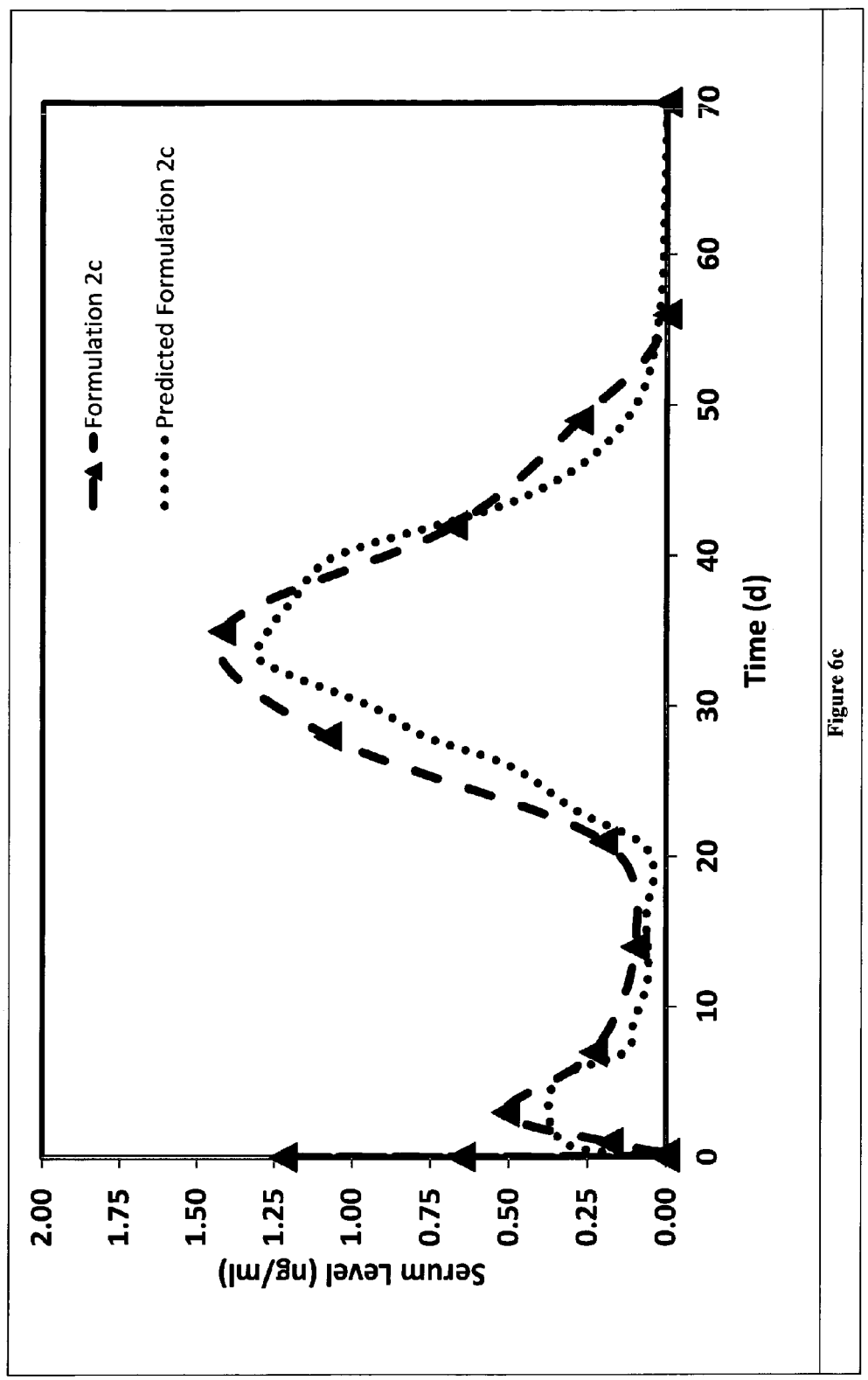

The final microspheres are analysed with respect to particle size, drug loading, polymer molecular weight, residual solvent and in vitro release as described below. The results are summarized in Tables 1 and 2 and also in FIGS. 3-4. Selected formulations (i.e., 1a and 2c) along with the reference product Sandostatin LAR have been tested in rats to establish an in vitro in vivo correlation model. The details of the PK study and the applied methodology for the development and the external are provided below. The in vivo results are provided in FIGS. 5-6.

Particle Size Distribution (PSD) Analysis

Particle side distribution was measured by laser diffraction using a Malvern Master Sizer 2000 Hydro2000S. The average particle size is expressed as the volume mean diameter in microns.

Determination of Drug Loading

About 50 mg of microspheres were completely dissolved in 10 ml methylene chloride (30 min sonication). 20 ml of 0.1M acetate buffer (pH 4.0) was added to the solution for extraction of octreotide into an aqueous phase. The two phases were thoroughly mixed by vortexing for 5 min then separated by centrifugation at 4000 rpm for 5 min. The aqueous phase was sampled for HPLC analysis to measure the content of octreotide. The sample was filtered through a 0.45 μm syringe filter before analysis. The HPLC conditions were as follows: gradient separation was performed with an Inertsil ODS3 column (4.6×250 mm, particle size 5 μm); the mobile phase consisted of 0.1% trifluoroacetic acid (TFA) in distilled water (eluent A) and 0.1% TFA in acetonitrile (eluent B) and was run with a linear gradient from 20% to 35% eluent B for 18 min. The flow rate was 1.0 ml/min, the injection volume was 10 μl and the detection wavelength was 210 nm.

Mean Molecular Weight Measurement

The molecular weight of microspheres was determined by gel permeation chromatography (GPC) using an Agilent Model GPC 50Plus system equipped with 2 columns PLgel 5 µm Mixed-D 300×7.5 mm connected in series and a refractive index (RI) detector. The mobile phase is THF with a flow rate of 1 ml/min and the temperature of the column is 30° C. For the analysis of the samples, 10-15 mg of microspheres are dissolved in 5 mL THF and the solution is left overnight under stirring. 2 ml are withdrawn, filtered through a 40 µm PTFE filters and analysed. The injection volume is 100 µL. The data collection and analysis was performed using Cirrus software. Polystyrene standards with MW range between 162 and 371100 are used for calibration.

In Vitro Release Method

About 150 mg of the formulated microspheres were placed in a 100 ml bottle and incubated in 30 ml acetate buffer (1 mM, pH 4.0) at 37° C. in a shaking bath (85 rpm). The release medium was sampled at various time points, filtered through a 0.45 µm syringe filter and analyzed via HPLC. The HPLC conditions were as follows: gradient separation was performed with an Inertsil ODS3 column (4.6×250 mm, particle size 5 µm); the mobile phase consisted of 0.1% trifluoroacetic acid (TFA) in distilled water (eluent A) and 0.1% TFA in acetonitrile (eluent B) and was run with a linear gradient from 25% to 35% eluent B for 25 min. The flow rate was 1.0 ml/min, the injection volume was 10 µl and the detection wavelength was 210 nm.

Residual Solvents (Dichloromethane)

It was investigated whether ethanol and/or methylene chloride are removed from Octreotide micro-particles. Micro-particles are totally dissolved in dimethyl sulfoxide (DMSO). Therefore, concentrations of ethanol and methylene chloride in the organic solution were quantitated by gas chromatography (GC). An amount of 90 mg of fresh microparticles were dissolved in 5 mL of dimethyl sulfoxide in a GC vial before headspace GC analysis. The residual solvents evaporation was achieved by a 30 min sample incubation at 100° C. in the GC oven. GC analysis was performed with GC-2010 plus (Shimadzu, Japan). An RTX-5 (RESTEK, USA) analysis column using Crossbond 5% diphenyl/95% dimethyl polysiloxane as stationary phase was used. The quantity of solvents was measured using calibration curve standards. The retention time of dichloromethane is 5.75 min Animal Studies Microsphere formulations after mixing with crystalline mannitol (i.e., 17% mannitol with respect to the total weight) were subjected to sterilization by UV radiation at 365 nm for 180 min using a 6 Watt UV light source in order to be used in pharmacokinetic studies in male Sprague-Dawley rats. Rats (six per group) weighing about 240-250 grams and of age 8-12 weeks were injected with the test formulations. Prior to injection, the dry powder samples were suspended in a sterile solvent (vehicle) consisting of water for injection, sodium carboxymethylcellulose 0.5% wt. and mannitol 0.6% wt. Animals were administered one single intramuscular injection in fixed dose of about 60 mg octreotide formulation (microspheres)/rat that corresponds to 3 mg octreotide active substance/rat in a volume of 0.25 ml/rat of a vehicle, into a single site. The suspension was administered via a hypodermic needle of 26 G intramuscularly into the rat's quadriceps muscle located on the cranial aspect of the femur. Rat blood samples were collected before drug dosing and thereafter at predetermined time points including 0.5 h, 1 h, 2 h, 6 h, 24 h, Day 3, 7, 14, 18, 21, 28, 35, 42, 49, 56 and Day 70 post-dose. At each time point, approximately 0.5 ml of blood were withdrawn from retro-orbital plexus under light isoflurane anesthesia and transferred into labeled tubes containing 200 mM $K_2EDTA$ as anticoagulant and mixed by manual inversion 4-5 times. The blood samples were kept on wet ice at all times and the plasma was separated by centrifugation within 1 h of sample collection. The plasma samples were stored below −60° C. until bioanalysis using a validated LC-MS/MS method.

In Vitro In Vivo Correlation

For the development of the IVIVC model, the below procedure was followed: (1) selection of formulations with different release rates including Sandostatin LAR, formulation 1a and formulation 2c, (2) measurement of in vitro dissolution profiles by various dissolution methods, (3) measurement of the PK in vivo plasma concentration profiles of the formulations (i.e., Sandostatin LA, formulation 1a and formulation 2c) after a single intramuscular administration in rats, (4) estimation of the in vivo release profile by the measured plasma concentration profiles using the Wagner-Nelson (one-compartment model) deconvolution technique, (5) calculation of the correlation between the deconvoluted in vivo release profile and the in vitro dissolution profiles using the pooled data of Sandostatin LAR and formulation 1a, (6) selection of the appropriate dissolution method with the higher correlation to in vivo data and establishment of the IVIVC by applying linear regression analysis (6) internal validation of the established model by comparing the back-calculated plasma concentration profiles using Wagner-Nelson convolution model for formulation Sandostatin LAR and formulation 1a and (7) external validation of the established model by comparing the predicted plasma concentration calculated by the in vitro dissolution profile of formulation 2c and the established model and the observed in vivo plasma concentration profile of formulation 2c.

Example 1a-c (Single Emulsion)

4 g of poly(D,L-lactide-co-glycolide) with a molar ratio of 50:50 (Mw=41,000 and polydispersity ca 1.65), commercially available from PURAC under the name PURASORB 5004A, was dissolved in 30 g of dichloromethane with magnetic stirring. The polymer solution is cooled down to 5° C. 0.2941 g of octreotide acetate was dissolved in 0.5882 g of water for injection with mixing. The octreotide acetate solution was added to the polymer solution and emulsified by mean of an Ultra Turrax® for 1 minute at 20,000 rpm to form the first emulsion (DP-dispersed phase). 11.5 g of poly(vinyl alcohol) EMROVE® 18-88 by Merck were dissolved in 2307 g of water for injection at 80° C. followed by the addition of 17.46 g of disodium hydrogen phosphate and 4.18 g of potassium dihydrogen phosphate. The solution was cooled down to 5° C. forming the continuous phase (CP). Microspheres of the desired particle size distribution were prepared by delivering the CP at 2.3 L/min and the DP at 15.6 mL/min, into an in-line Kinematica MT 3000 disperser. The microsphere suspension was received in a double-jacketed glass reactor vessel, controlled at 20° C. and with vigorous stirring, in order to remove the solvent. The temperature in the vessel was increased to 38° C. according to predefined time intervals as presented in the following table (Table 1). After 4 hours the microspheres were transferred to a glass filter dryer, washed with an excess of water at room temperature and left at 10 mbar vacuum and under gently stirring for 24 hours to dry.

TABLE 1

Properties of 1a-1c formulations

| Formulation | Time 20-38° C. (min) | Drug Loading (%) | $M_w$ (g/mol) | Particle size distribution | Residual DCM (%) | Total Impurities (%) | Dissolution | |
|---|---|---|---|---|---|---|---|---|
| Sandostatin LAR ® | 5.0 | 64,200 | | d(0.1) 36.7 d(0.5) 50.7 d(0.9) 69.8 | 0.30 | 3 | $x_0$ (Lag time) $y_0$ (Initial release) a (final release) b (Slope) | 25.4 4.3 90.0 6.28 |
| 1a | 20 | 4.83 | 39,600 | d(0.1) 27.56 d(0.5) 44.097 d(0.9) 71.158 | 0.31 | 2.23 | $x_0$ (Lag time) $y_0$ (Initial release) a (final release) b (Slope) | 22.1 0.4 77.4 2.6 |
| 1b | 60 | 5.15 | 40,200 | d(0.1) 29.907 d(0.5) 51.017 d(0.9) 84.049 | 0.26 | 1.29 | $x_0$ (Lag time) $y_0$ (Initial release) a (final release) b (Slope) | 25.8 0 82.0 2.3 |
| 1c | 180 | 4.85 | 40,850 | d(0.1) 31.148 d(0.5) 48.22 d(0.9) 74.301 | 0.18 | 1.95 | $x_0$ (Lag time) $y_0$ (Initial release) a (final release) b (Slope) | 31.5 0.4 80.6 2.2 |

Example 2a-c (Double Emulsion)

4 g of poly(D,L-lactide-co-glycolide) with a molar ratio of 50:50 (Mw=41,000 and polydispersity ca 1.65), commercially available from PURAC under the name PURASORB 5004A, was dissolved in 30 g of dichloromethane with magnetic stirring. The polymer solution is cooled down to 5° C. The polymer solution is sterilized by filtration through a syringe filter and cooled down to 5° C. 0.2941 g of octreotide acetate was dissolved in 2.941 g of methanol with mixing. The octreotide acetate solution was added to the polymer solution and mixed with stirring to form the oil phase (DP-dispersed phase). 11.5 g of poly(vinyl alcohol) EMROVE® 18-88 by Merck were dissolved in 2307 g of water for injection at 80° C. followed by the addition of 17.46 g of disodium hydrogen phosphate and 4.18 g of potassium dihydrogen phosphate. The solution was cooled down to 5° C. forming the continuous phase (CP). Microspheres of the desired particle size distribution were prepared by delivering the CP at 2.3 L/min and the DP at 18.7 mL/min, into an in-line Kinematica MT 3000 disperser. The microsphere suspension was received in a double-jacketed glass reactor vessel, controlled at 20° C. and with vigorous stirring, in order to remove the solvent. The temperature in the vessel was increased to 38° C. according to predefined time intervals as presented in the following table (Table 3). After 4 hours the microspheres were transferred to a glass filter dryer, washed with an excess of water at room temperature and left at 10 mbar vacuum and under gently stirring for 24 hours to dry.

TABLE 2

Properties of 2a-2c formulations

| Formulation | Time 20-38° C. (min) | Drug Loading (%) | $M_w$ (g/mol) | Particle size distribution | Residual DCM (%) | Total Impurities (%) | Dissolution | |
|---|---|---|---|---|---|---|---|---|
| Sandostatin LAR ® | | 5.0 | 64,200 | d(0.1) 36.7 d(0.5) | 0.30 | 3 | $x_0$ (Lag time) $y_0$ (Initial release) | 26.5 |

TABLE 2-continued

Properties of 2a-2c formulations

| Formulation | Time 20-38° C. (min) | Drug Loading (%) | $M_w$ (g/mol) | Particle size distribution | Residual DCM (%) | Total Impurities (%) | Dissolution |
|---|---|---|---|---|---|---|---|
|  |  |  |  | 50.7 d(0.9) 69.8 |  |  | 7.4 a (final release) 84.7 b (Slope) 5.2 |
| 2a | 20 | 4.79 | 41,050 | d(0.1) 26.682 d(0.5) 42.577 d(0.9) 68.198 | 0.23 | 2.22 | $x_0$ (Lag time) 19.4 $y_0$ (Initial release) 0 a (final release) 82.3 b (Slope) 4.2 |
| 2b | 60 | 4.8 | 39,780 | d(0.1) 28.281 d(0.5) 46.96 d(0.9) 76.958 | 0.38 | 1.52 | $x_0$ (Lag time) 23.7 $y_0$ (Initial release) 0 a (final release) 81.5 b (Slope) 3.9 |
| 2c | 180 | 5.03 | 40,230 | d(0.1) 28.644 d(0.5) 46.742 d(0.9) 75.041 | 0.19 | 0.85 | $x_0$ (Lag time) 31.7 $y_0$ (Initial release) 5.0 a (final release) 84.1 b (Slope) 3.9 |

The invention claimed is:

1. A process for the preparation of a poly(D,L lactide-co-glycolide) polymer microspheres of a peptide, which peptide can also be in the form of a pharmaceutically-acceptable salt, comprising:
   a. dissolving the peptide, or salt thereof, in at least one organic solvent miscible in water, and optionally containing also water, to form a water phase;
   b. forming an oil-in-water or water-in-oil-water emulsion in a suitable oil phase comprising an organic solution of the poly(D,L lactide-co-glycolide) polymer, the solution being non-miscible with the water phase, and wherein the organic solution of the poly(D,L lactide-co-glycolide) polymer is cooled down to 5° C. or below;
   c. evaporating the at least one organic solvent used in step a from the emulsion to form the microspheres by controlling the temperature during the evaporation step and increasing the temperature during the evaporation step; and controlling in-vivo and in-vitro release characteristics of the peptide by the increasing temperature rate during the evaporation step.

2. A process according to claim 1 wherein the peptide active substance is octreotide acetate.

3. A process according to claim 1 wherein the organic solvent is methanol and water is added.

4. A process according to claim 1 wherein the poly(D,L lactide-co-glycolide) polymer is dissolved in dichloromethane.

5. A process according to claim 1 wherein the evaporation in step c is initiated above 15° C. and during the evaporation step the temperature of the emulsion is raised to greater than 35° C.

6. A process according to claim 1, wherein the temperature is raised over a time period of 20 min to 3 hours.

7. A process according to claim 6 wherein further drying continues for an extended period after the period of temperature elevation.

* * * * *